(12) United States Patent
Allan et al.

(10) Patent No.: US 6,871,647 B2
(45) Date of Patent: Mar. 29, 2005

(54) INHALER

(75) Inventors: Robert David Allan, Greensborough (AU); Gregory Charles Pike, Dandenong (AU)

(73) Assignee: Advent Pharmaceuticals Pty Ltd, Mulgrave (AU)

( * ) Notice: Subject to any disclaimer, the term of this patent is extended or adjusted under 35 U.S.C. 154(b) by 1 day.

(21) Appl. No.: 10/275,478

(22) PCT Filed: Sep. 18, 2002

(86) PCT No.: PCT/AU02/01284

§ 371 (c)(1),
(2), (4) Date: Nov. 6, 2002

(87) PCT Pub. No.: WO03/024514

PCT Pub. Date: Mar. 27, 2003

(65) Prior Publication Data

US 2003/0178024 A1 Sep. 25, 2003

(51) Int. Cl.⁷ .............................................. A61M 15/00
(52) U.S. Cl. .............................. 128/203.21; 128/203.15
(58) Field of Search ..................... 128/200.14, 200.12, 128/200.23, 203.12, 203.15, 203.13, 203.21; 604/58

(56) References Cited

U.S. PATENT DOCUMENTS

| | | |
|---|---|---|
| 4,627,432 A | 12/1986 | Newell et al. |
| 4,778,054 A | 10/1988 | Newell et al. |
| 4,811,731 A | 3/1989 | Newell et al. |
| 5,408,994 A | 4/1995 | Wass et al. |
| 5,469,843 A | 11/1995 | Hodson |
| 5,622,166 A | 4/1997 | Eisele et al. |
| 5,881,719 A * | 3/1999 | Gottenauer et al. ..... 128/203.15 |
| 5,915,378 A * | 6/1999 | Lloyd et al. ........... 128/200.22 |
| 5,921,237 A | 7/1999 | Eisele et al. |
| 6,029,663 A | 2/2000 | Eisele et al. |
| 6,065,472 A * | 5/2000 | Anderson et al. ....... 128/203.21 |
| 6,116,237 A | 9/2000 | Schultz et al. |
| 6,116,238 A | 9/2000 | Jackson et al. |
| 6,273,085 B1 | 8/2001 | Eisele et al. |

FOREIGN PATENT DOCUMENTS

| | | |
|---|---|---|
| AU | 200048848 B2 | 10/2000 |
| GB | 2 242 134 A | 9/1991 |
| WO | WO 98/03217 | 1/1998 |
| WO | WO 99/27987 | 6/1999 |
| WO | WO 01/34234 A1 | 5/2001 |
| WO | WO 02/24263 A2 | 3/2002 |
| WO | WO 0224263 A2 * | 3/2002 |

\* cited by examiner

Primary Examiner—Aaron J. Lewis
(74) Attorney, Agent, or Firm—Stites & Harbison, PLLC; Ross F. Hunt, Jr.

(57) ABSTRACT

An inhaler for delivering metered doses of powdered medicament, the inhaler having a plurality of compartments spaced in an array and each arranged to contain a metered dose of the medicament, a lever to displace the compartments one by one into line with an inhalation aperture that constitutes a mouthpiece, each compartment including inner and outer edges, the plurality of compartments being closed by a sealing layer, the inhaler further having a mechanism adapted to lift the sealing layer off the inner and outer edges of the compartment to open an air passageway defined by the compartment and the sealing layer so that, in use, on inhalation through the mouthpiece, air flow in the air flow passageway picks up and entrains the powder in the compartment to be drawn with the air out of the inhaler through the mouthpiece.

66 Claims, 18 Drawing Sheets

DETAIL A
SCALE 5 : 1

DETAIL A
SCALE 5:1

INHALER

BACKGROUND OF THE INVENTION

There are many types of inhalers that can provide delivered metered doses. The majority of inhalers of this kind are designed to provide multiple doses. It is however known that inhalers of this kind can also be used to provide a single dose.

In situations where a metered dose is to be dispensed it is important that the inhaler always dispenses the exact dose. There is also a problem with inhalers of this kind if there is a tendency to allow unintentional additional dosing. Inhalers need to be small, compact, easy to use and yet not too expensive. The inhalers also need to satisfy safety criteria set down by appropriate standards.

It is these issues that have brought about the present invention.

SUMMARY OF THE INVENTION

In accordance with one aspect of the present invention there is provided an inhaler for delivering metered doses of powdered medicament, the inhaler having a plurality of compartments spaced in an array and each arranged to contain a metered dose of the medicament, means to displace the compartments one by one into line with an inhalation aperture that constitutes a mouthpiece, each compartment including inner and outer edges, the plurality of compartments being closed by a sealing layer, means to lift the sealing layer off the inner and outer edges of the compartment to open an air passageway defined by the compartment and the sealing layer so that, in use, on inhalation through the mouthpiece, air flow in the air flow passageway picks up and entrains the powder in the compartment to be drawn with the air out of the inhaler through the mouthpiece.

In accordance with another aspect of the present invention there is provided a disposable cartridge adapted to be received in a body of an inhaler, the cartridge having a plurality of compartments spaced in an array and each arranged to contain a metered dose of medicament, the compartments being displaceable one by one into line with an outlet aperture, each compartment including inner and outer edges, the plurality of compartments being closed by a sealing layer, means to lift the sealing layer off the inner and outer edges of the compartment to open an air passageway defined by the compartment and the sealing layer so that, in use, air flow in the air flow passageway picks up and entrains the powder in the compartment to be drawn with the air out of the cartridge through the outlet aperture.

DESCRIPTION OF THE DRAWINGS

Embodiments of the present invention will now be described by way of example only in which.

DESCRIPTION OF THE PREFERRED EMBODIMENTS

Figure 1:
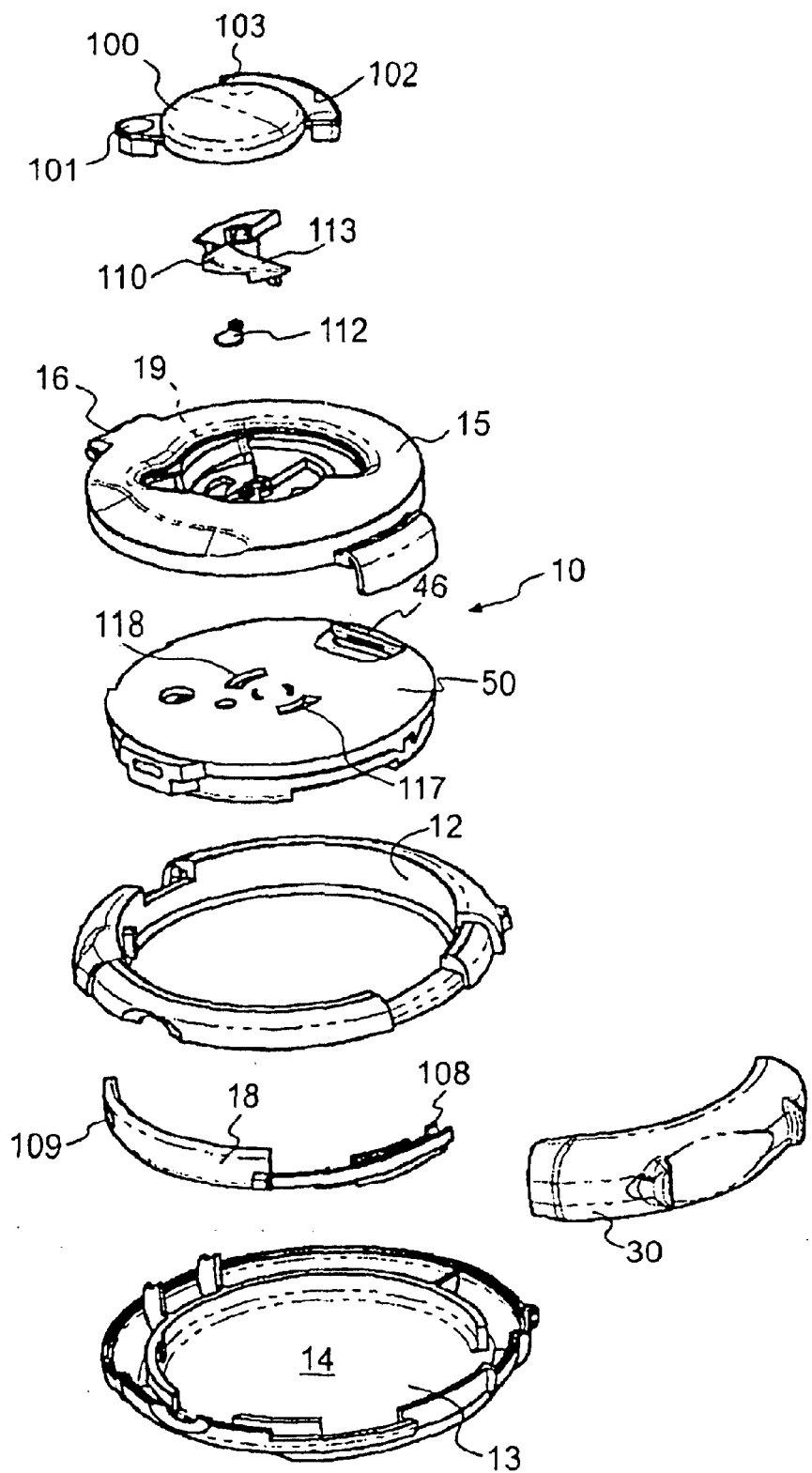
FIG. 1 is an exploded view perspective view of an inhaler in accordance with a first embodiment of the invention.

As shown in the exploded view of FIG. 1 an inhaler 10 comprises a disposable medicament cartridge 50 that is located in an inhaler body 11 that includes an upper body 12, lower body 13 that fit together to support a drive cam 18 and lever 30 and define a recess 14 into which the cartridge 50 fits. The body 11 is closed by a lid 15 that is hinged to one side 16 of the body 11. The upper surface of the lid supports a window 100, air entry inlet 19 and air entry indicator 110 and a one way valve 112.

Figure 2A:
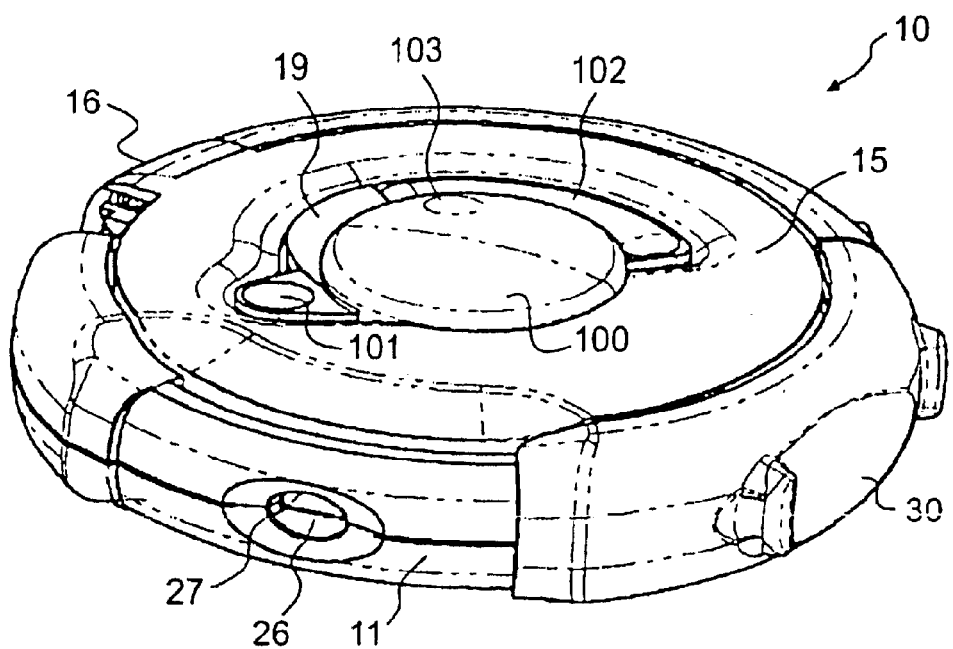
FIGS. 2A & 2B are perspective views of the inhaler.
Figure 2B:
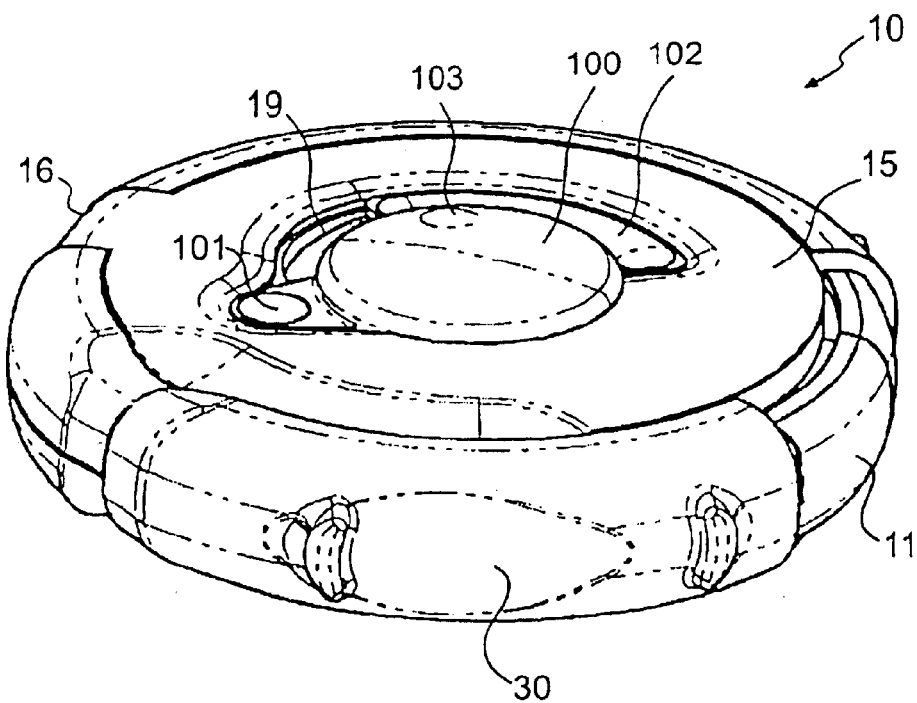

As shown in FIG. 2, the inhaler 10 is substantially circular in plan and has a mouthpiece 26 having an inhalation aperture 27 positioned in the body periphery on one side with the displacement lever 30 located on that side to be displaceable relative to the body 11 between the open position shown in FIG. 2a to the closed position in which the lever 30 covers the mouthpiece 26 as shown in FIG. 2b.

Figure 4:
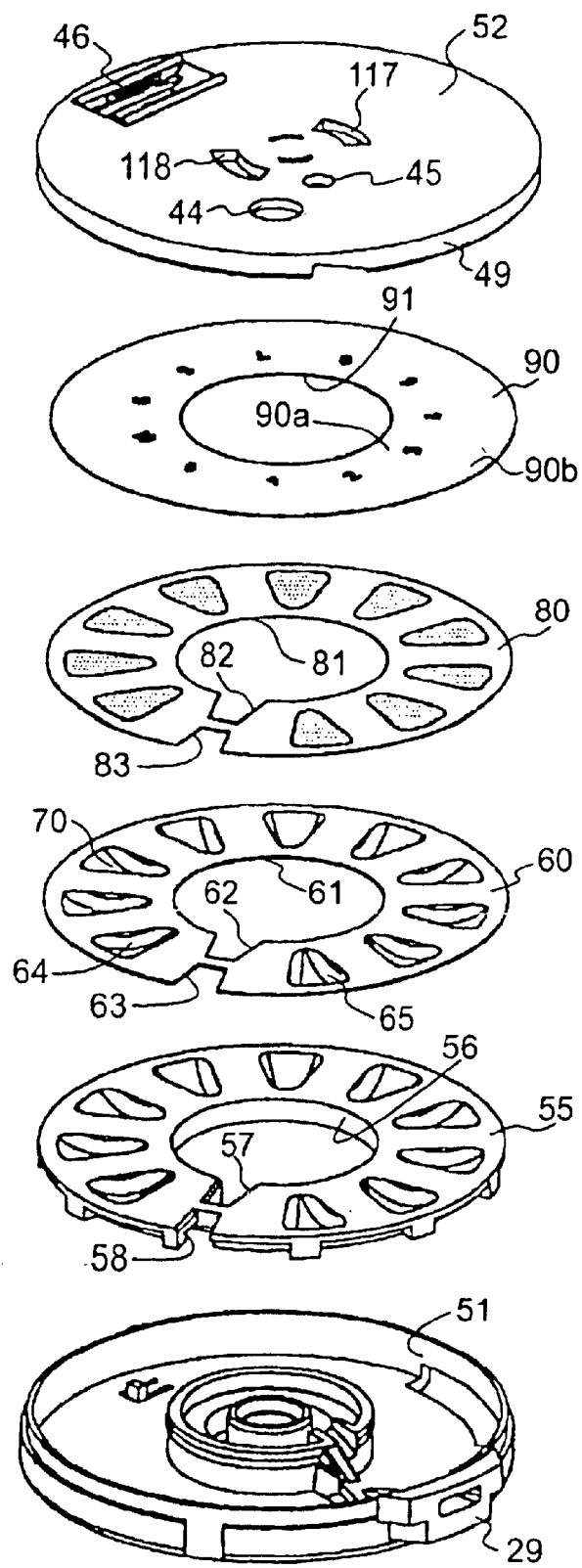
FIG. 4 is an exploded perspective view of the cartridge.
Figure 10:
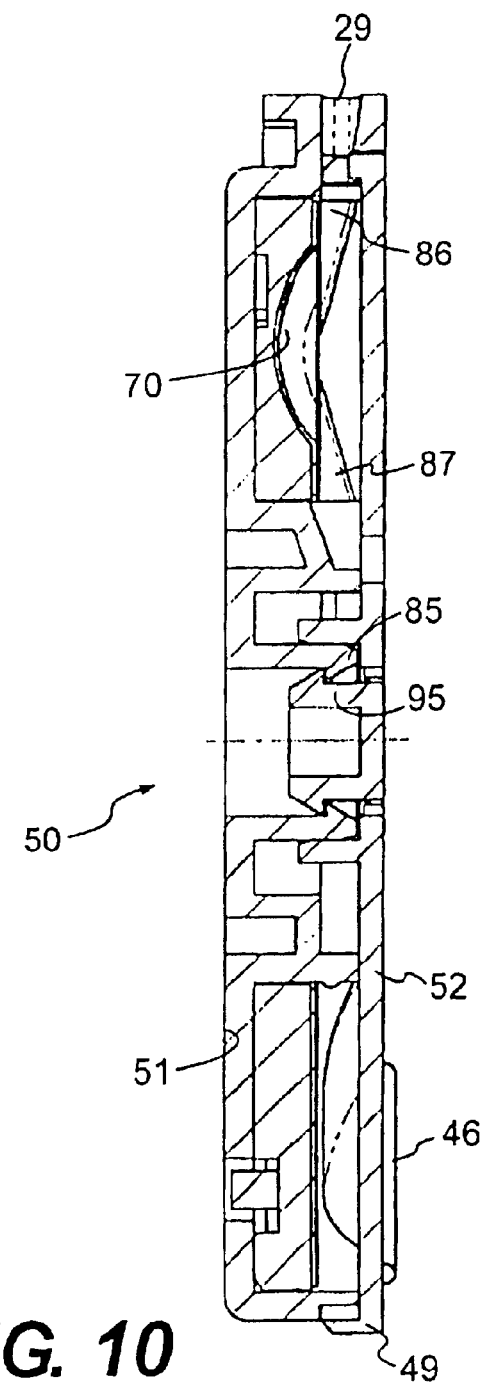
FIG. 10 is a cross sectional view taken along the lines A—A of FIG. 9.

The cartridge 50 is shown in greater detail in FIG. 4 and comprises a multi-layered annular disc assembly that is located between upper and lower covers 52, 51 that clip together as shown in FIG. 10. The upper cover 52 has an air inlet aperture 45 that communicates with the disc assembly to define an air passageway that exits the cartridge via slot 29 on the periphery of the lower cover 51. The disc assembly includes a cartridge base 55 that is of disc shape with a central aperture 56. The cartridge base 55 supports a, base foil 60 that has a central aperture 61 and contains ten recessed compartments 70 spaced around the periphery of the base foil 60. The compartments are equally spaced except that there is a wider gap between the first 64 and the last 65 compartments. The base 55 is formed with recesses that correspond to the compartments 70.

The base foil 60 is covered first by a perforated layer 80 which is in turn covered by a lidding foil layer 90. Both the perforated layer and lidding foil 80 and 90 have internal apertures 81 and 91. The apertures 56, 61, 81 in the cartridge base 55, base foil 60 and perforated layer 80 include a cut-out 57, 62 and 82 that is radially aligned with a cut-out 58, 63, and 83 in the outer periphery. The lidding foil 90 is securely bonded to the perforated layer 80 which is attached to the base foil 60 to seal the compartments 70 once filled with medicament powder.

Figure 5:
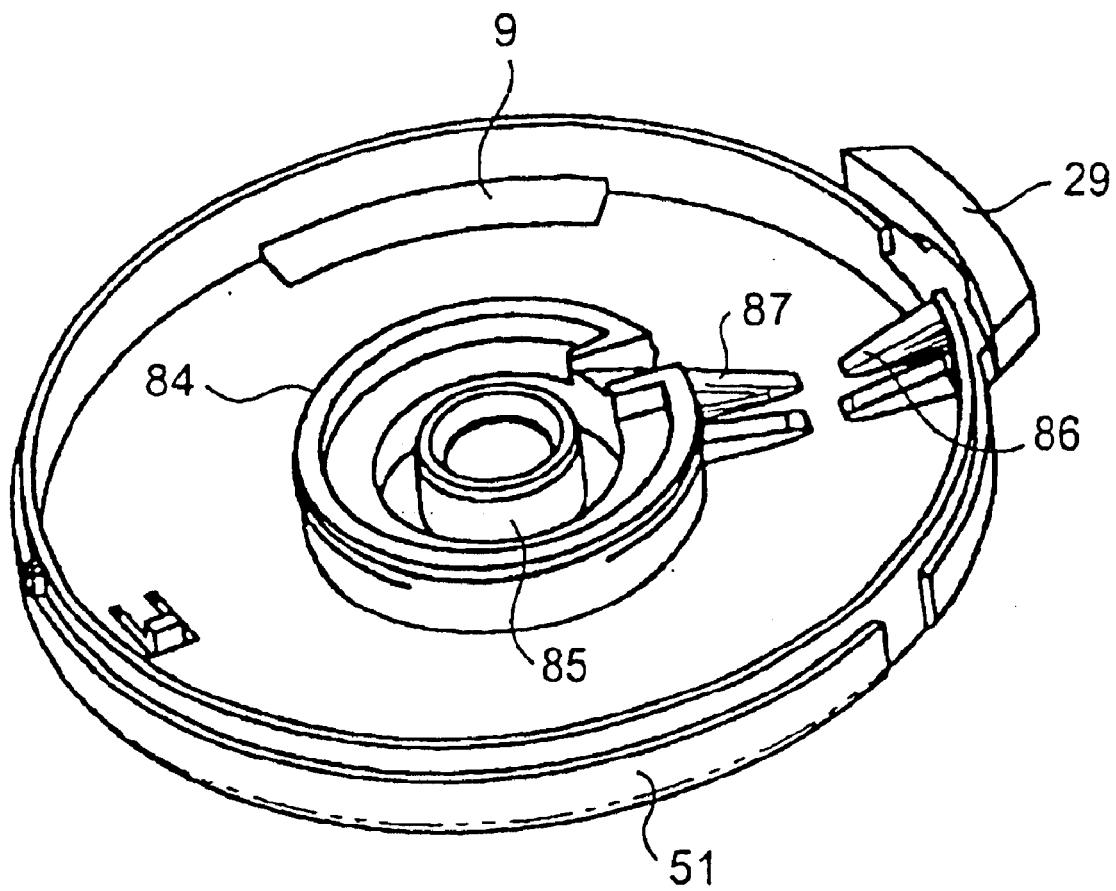
FIG. 5 is a perspective view of a lower cover of the cartridge.

The cartridge 50 is designed to hold a plurality of metered doses of powdered medicament in separate sealed compartments 70 and the operation of the lever 30 displaces the drive cam 18 which rotates components of the cartridge 50 to expose individual doses to the air passageway that is in communication with the mouthpiece 26. As shown in FIG. 5, the cartridge 50 includes openers 86, 87 located in the lower cover 51 that operates to expose a single dose by unsealing each compartment 70 so that when the user inhales through the mouthpiece 26 air is drawn through an aperture in the lid 15 of the inhaler 10 through the inlet aperture of the cartridge, across the unsealed compartment 70 to pick up the powder in the compartment 70 for delivery to the mouthpiece 26 via the outlet slot 29. The cartridge 50 can be disposed of and be replaced by a new cartridge when all or part of the compartments 70 of the powered medicament have been emptied. The inhaler is in consequence reusable. The cartridge may be removed or reinserted as required.

Figure 6:
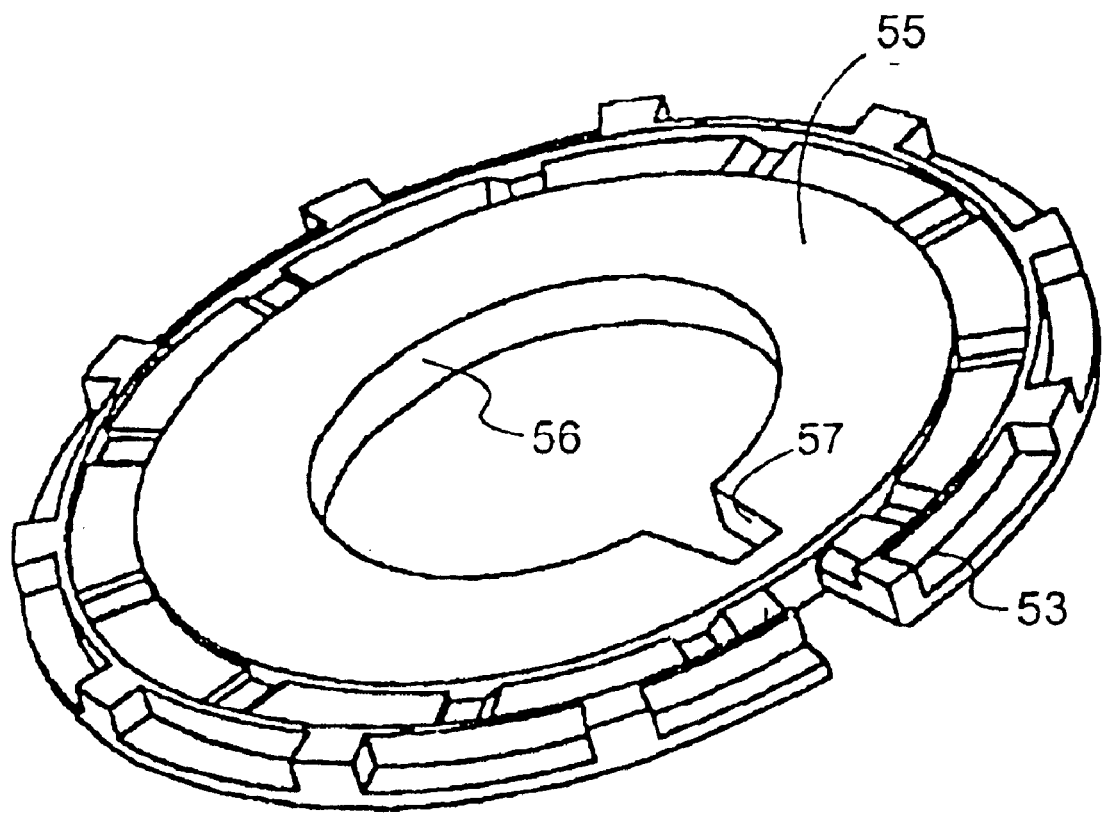
FIG. 6 is a perspective view of the underside of a base of the cartridge.

As shown in FIG. 6, the underside of the periphery of the cartridge base 55 is provided with a plurality of equally spaced cutouts 53, that are adapted to be engaged by the drive cam 18 driven by the lever 30 to cause the cartridge base 55, base foil 60, perforated layer 80, lidding foil 90 and upper cover 52 to be rotated through a small angle when the lever 30 is displaced in the anti-clockwise direction. The upper cover 52 is also rotated by the drive cam 18 through a small angle when the lever 30 is displaced in the clockwise direction.

It is however understood that more or less than ten compartments 70 can be positioned on the base foil 60 and the cartridge base 55 can include as many peripheral cutouts as are necessary to ensure that each compartment is indexed to the required position by displacement of the lever 30. The base foil 60 is positioned axially aligned on top of the cartridge base 55.

Figure 7:
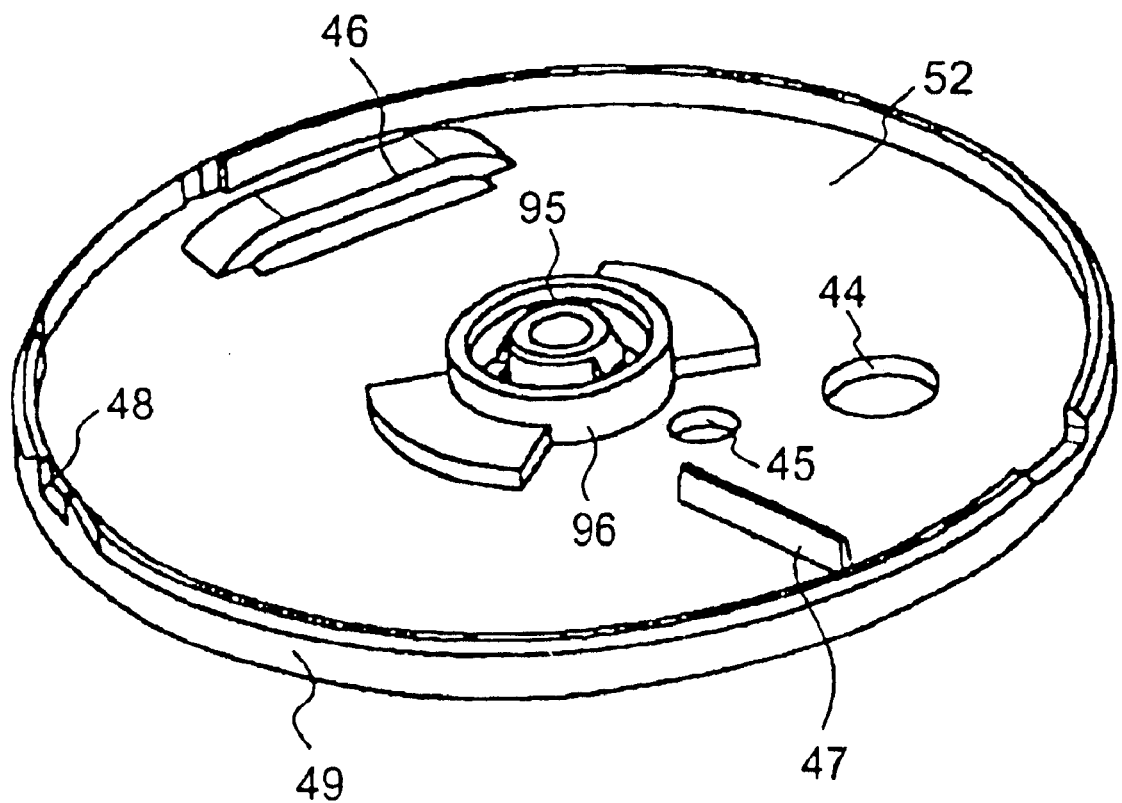
FIG. 7 is a perspective view of the underside of a upper cover of the cartridge.
Figure 8A:
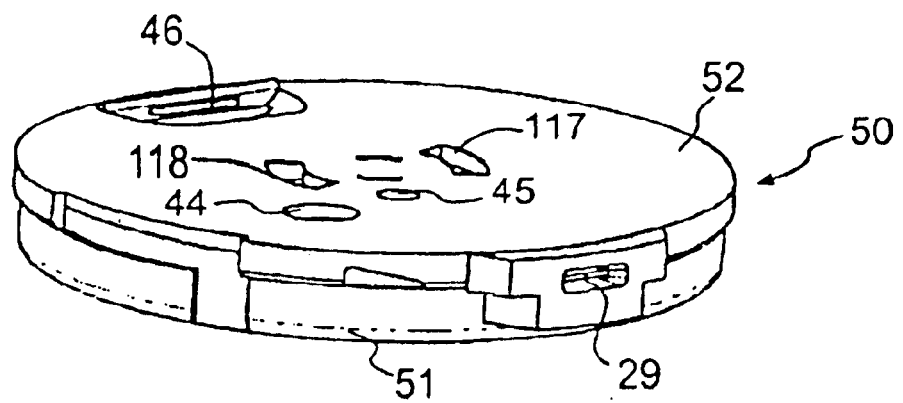
FIGS. 8a and 8b are perspective views of the assembled cartridge viewed from the top.
Figure 8B:
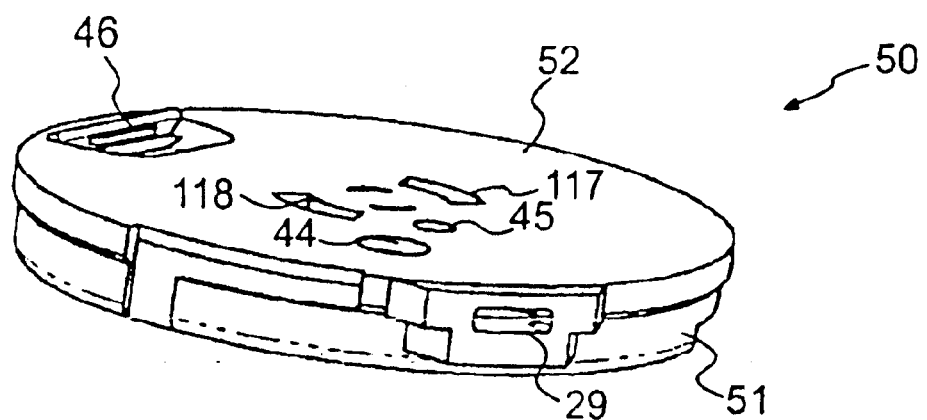
Figure 9:
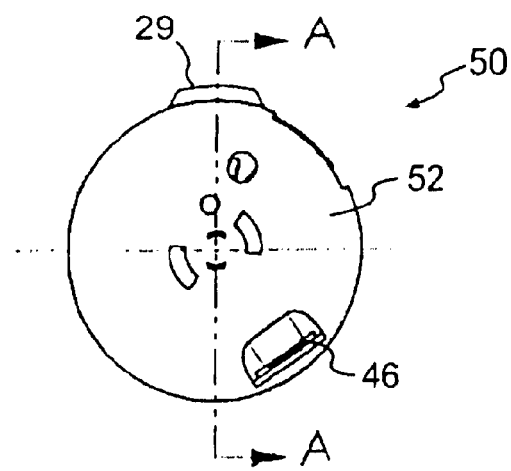
FIG. 9 is a plan view of the cartridge.

The lower cover 51 has an arcuate slot 9 through which the drive cam 18 extends to engage the cartridge base. The lower cover 51 of the cartridge 50 has a central upstanding circular spigot 84 that includes an internal upstanding ring 85. As shown in FIGS. 4 and 5 a pair of radially aligned wedges 87 and 86 extend outwardly and inwardly from the spigot 84 and inner wall of the lower cover 51. When the base foil compartments 70 have been filled and covered by the perforated layer 80 and sealed by the lidding foil 90, the laminated cartridge assembly is lowered into the lower cover 51 with the wedge shaped openers 87, 86 clearing the inner and outer slots 57, 58, 62, 63, 82 & 83 on the central apertures and outer peripheries of the base, base foil and perforated layers respectively. It should be noted that the lidding foil layer 90 does not have slots on the inner and outer peripheries which means that the foil rests on the wedges 86, 87. The cartridge 50 is completed by location of the upper cover 52 into locked engagement with the lower cover 51. As shown in FIG. 7, the upper cover 52 has a peripheral downwardly extending skirt 49 with a rectangular cut-out 48 into which a lug 108 on the end of the drive cam 18 locates so movement of the drive cam 18 causes a rotational movement of the upper cover 52.

As shown in FIGS. 7 and 10, the upper cover 52 has a central tapered boss 95 that clips into the ring 85 in the lower cover 51. A downwardly extending annular flange 96 fits against the exterior of the ring 85 allowing the upper cover 52 to oscillate relative to the lower cover 51. The upper surface of the upper cover 52 includes a viewing aperture 44 and an air inlet aperture 45. A finger tab 46 extends down from the upper surface of the cover to provide ease of removal of the cartridge 50 from the inhaler body. The underside of the upper cover 52 also has an elongate downwardly extending bar 47 that, in use, engages the top of the lidding foil 90 to push back the lidding foil onto the perforated layer 80, base foil 60 and base 55 after the contents of a compartment have been ejected. The bar 47 thus partially reseals the compartment.

Figure 3:
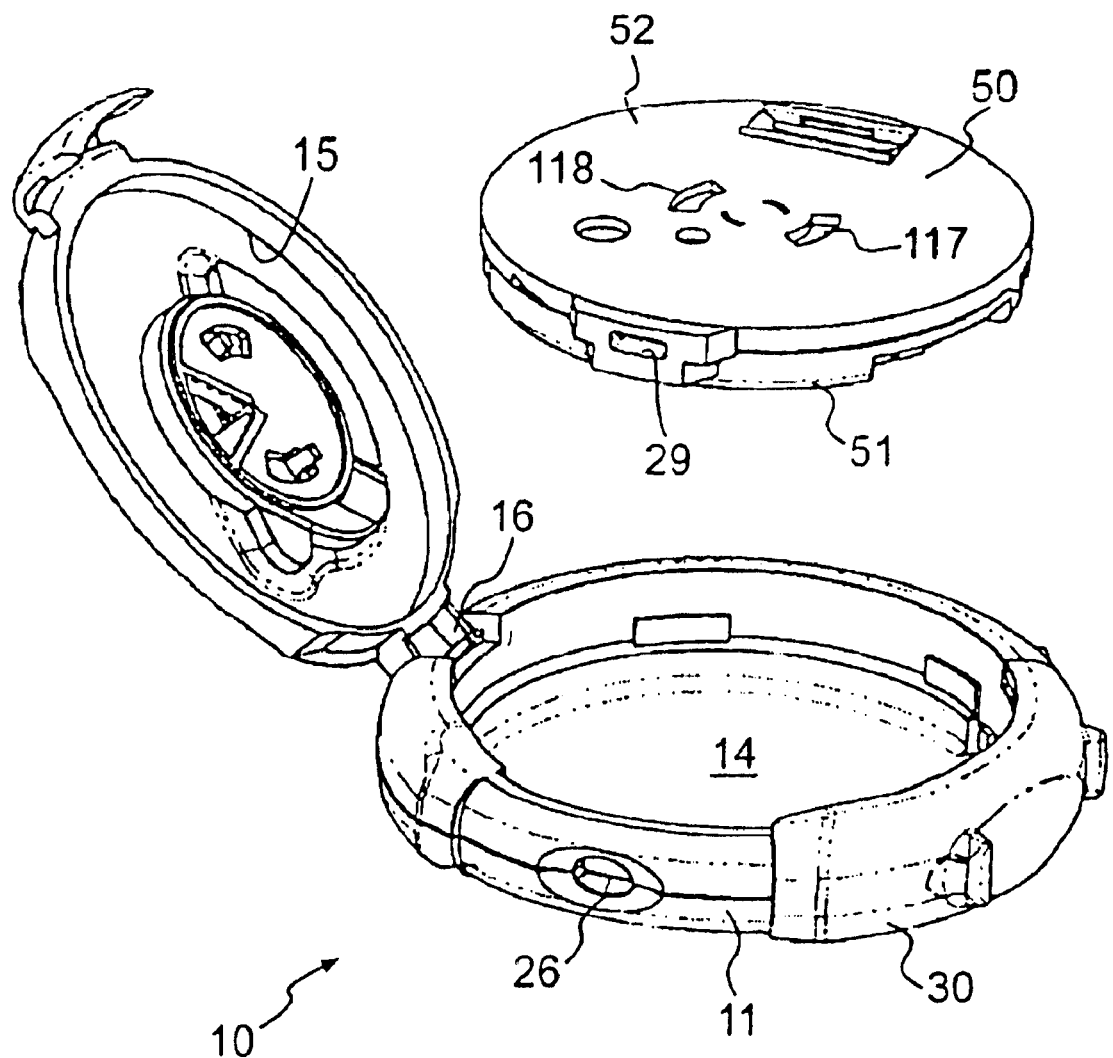
FIG. 3 is an exploded perspective view of the inhaler that shows a lid of the inhaler in an open position with a cartridge outside the inhaler.

FIG. 3 shows how the cartridge 50 can be lowered into the inhaler body 11. The cartridge 50 is gripped by the finger tab 46 and lowered into the recess 14 of the inhaler body 11 with outlet slot 29 aligned with the mouthpiece 26. The shape of the cartridge 50 is such that it can only be positioned in the inhaler in the correct position. The lever 30, through the drive cam (not shown), engages the cutouts 53 in the underside of the cartridge base 55 so that movement of the lever 30 has the effect of causing rotational movement of the disc base 55. The lever that drives the cartridge base 55 to rotate relative to the lower cover 51 of the cartridge 50 also has the effect of causing the upper cover 52 to oscillate on the lower cover 51 by contact between the lug 108 on the drive cam 18 and the cut-out 48 in the upper cover 52. The connection between the lever 30 and drive cam 18 introduces a small degree of free play or neutral movement.

Figure 11:
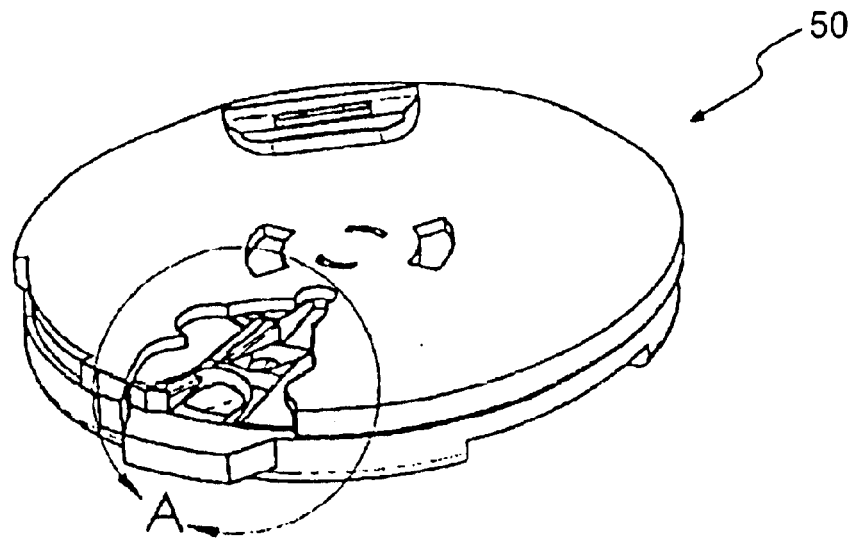
FIG. 11 is a perspective view of the cartridge with part cutaway showing an open compartment.
Figure 11A:
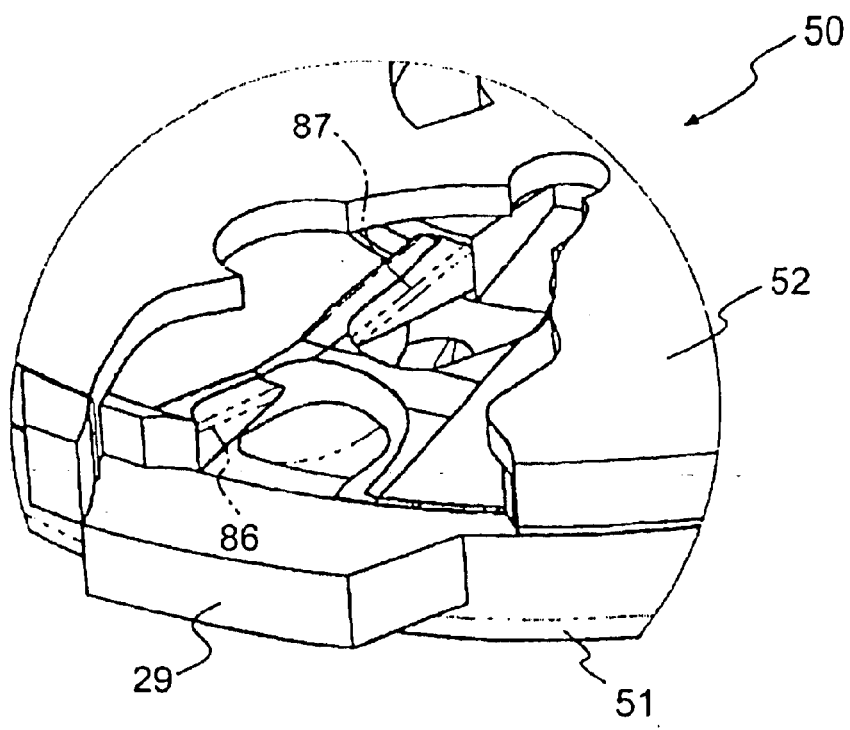

The role of the wedge shaped openers 86, 87 is illustrated with particular reference to FIGS. 10 and 11. As mentioned above, when the cartridge is assembled, the disc assembly sits in the lower cover 51 with the wedge shaped openers 86, 87 resting against the underside of the lidding foil layer 90. As the lever is actuated to cause the disc assembly to rotate relative to the lower cover 51, the inclined ramp on the upper surface of the openers 86, 87 has the effect of partially lifting the lidding foil 90 at the inner and outer sections from the top of the perforated layer 80 thereby exposing the powder within the compartment 70. The inner and outer sections or portions of the lidding foil 90 are indicated at 90a and 90b, respectively, in FIG. 4. The openers can either be positioned in a leading, central or trailing position in relation to the medicament compartment 90 on the assembly and as the disc continues to rotate, the openers lift the inner and outer sections of the lidding foil to expose the contents for removal upon inhalation and then allow the lidding foil to fall back into position against the perforated layer 80 thereby re-closing the compartment 70. The trailing bar 47 on the underside of the upper cover 52 then pushes the foil back against the base foil to partially reseal the compartment.

Figure 12:
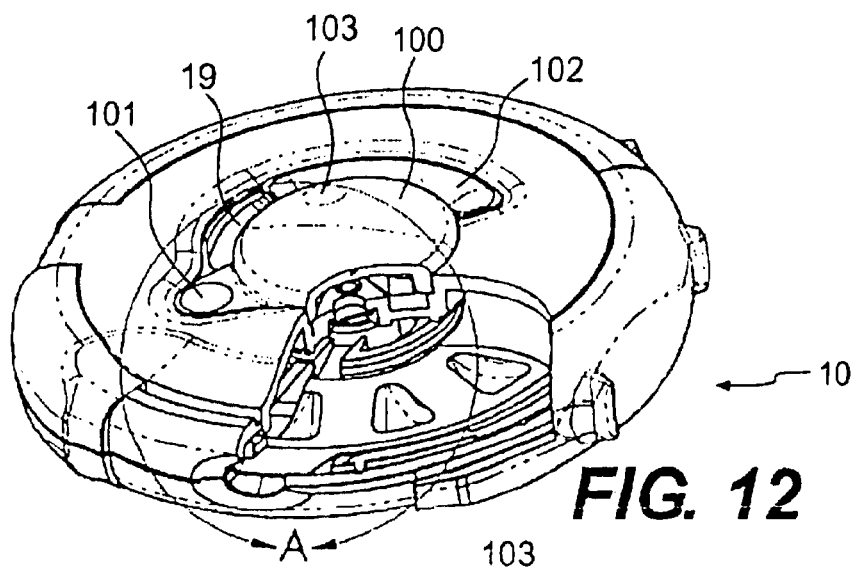
FIG. 12 is a perspective view with part cut away of the assembled inhaler showing the air passageway.
Figure 12A:
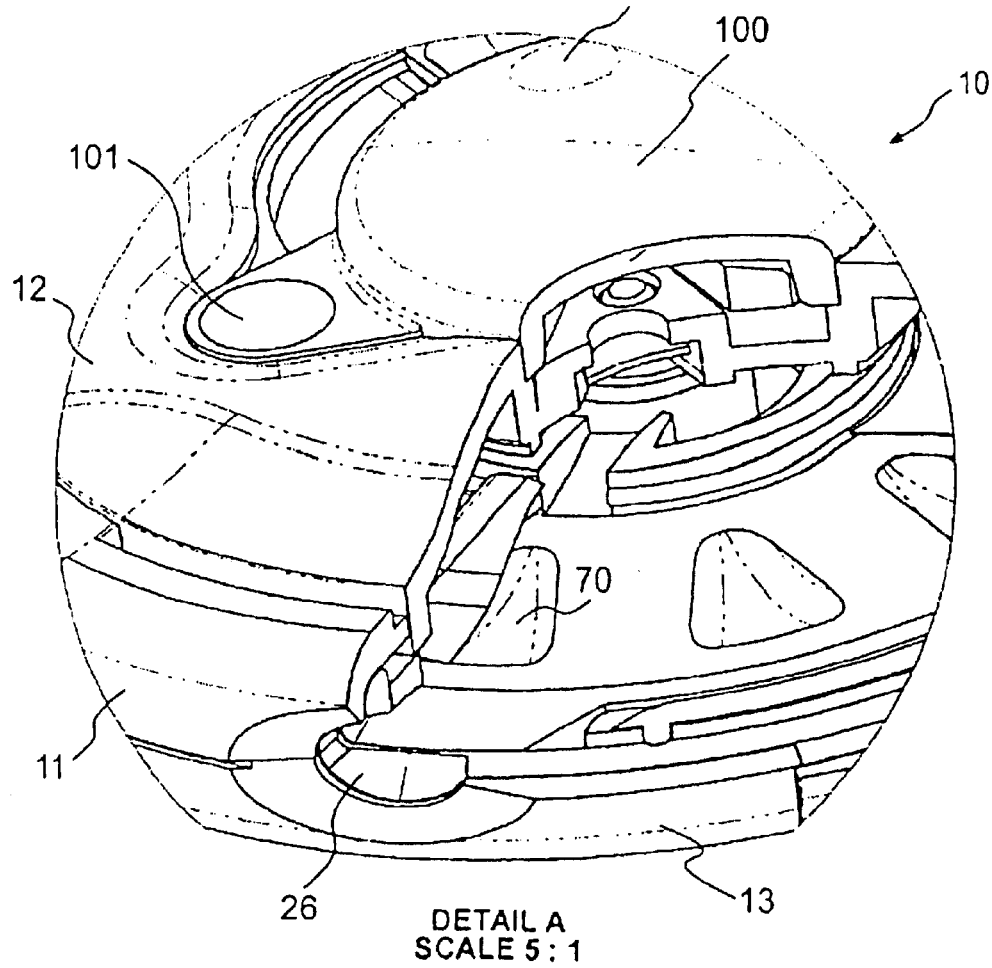
Figure 13A:
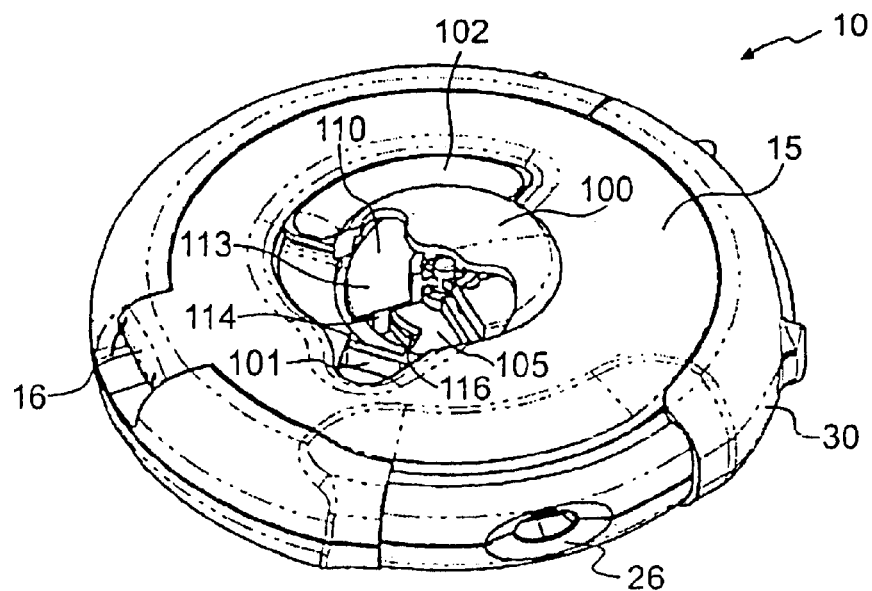
FIGS. 13a and 13b are perspective views of the top of the inhaler with part of a cover cut away, and FIG. 14 are perspective views of the underside of the lid of the inhaler.

The lid 15 of the inhaler is shown in greater detail in FIGS. 2, 12 and 13. The lid has a circular shaped clear cover 100 with a viewing tab 101 on one side and an arcuate window 102 on the opposite side. The circular shaped clear cover 20 is obscured except for an area 103. There is a gap extending about 90° around the clear cover 100 defining the air inlet 19. The underside of the lid has a central spigot 104 which supports a flow indicator 110 and a flap valve 112. As air is drawn into the inhaler through the air inlet 19, the flexible flap valve 112 pivots open as shown in detail B. Any attempt to blow air back through the inhaler is prevented by the flap valve 112 moving to the closed position shown in detail A.

Figure 13B:
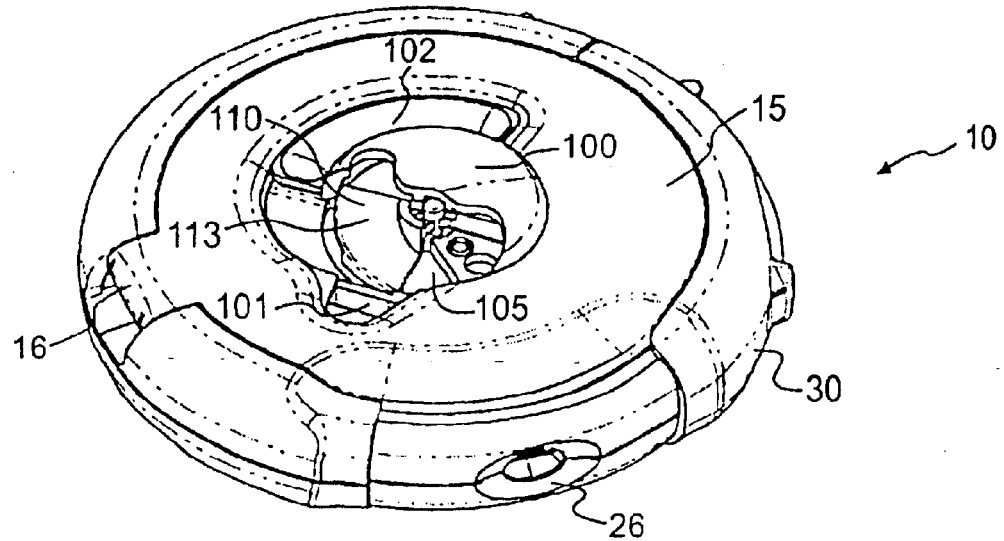
Figure 14:
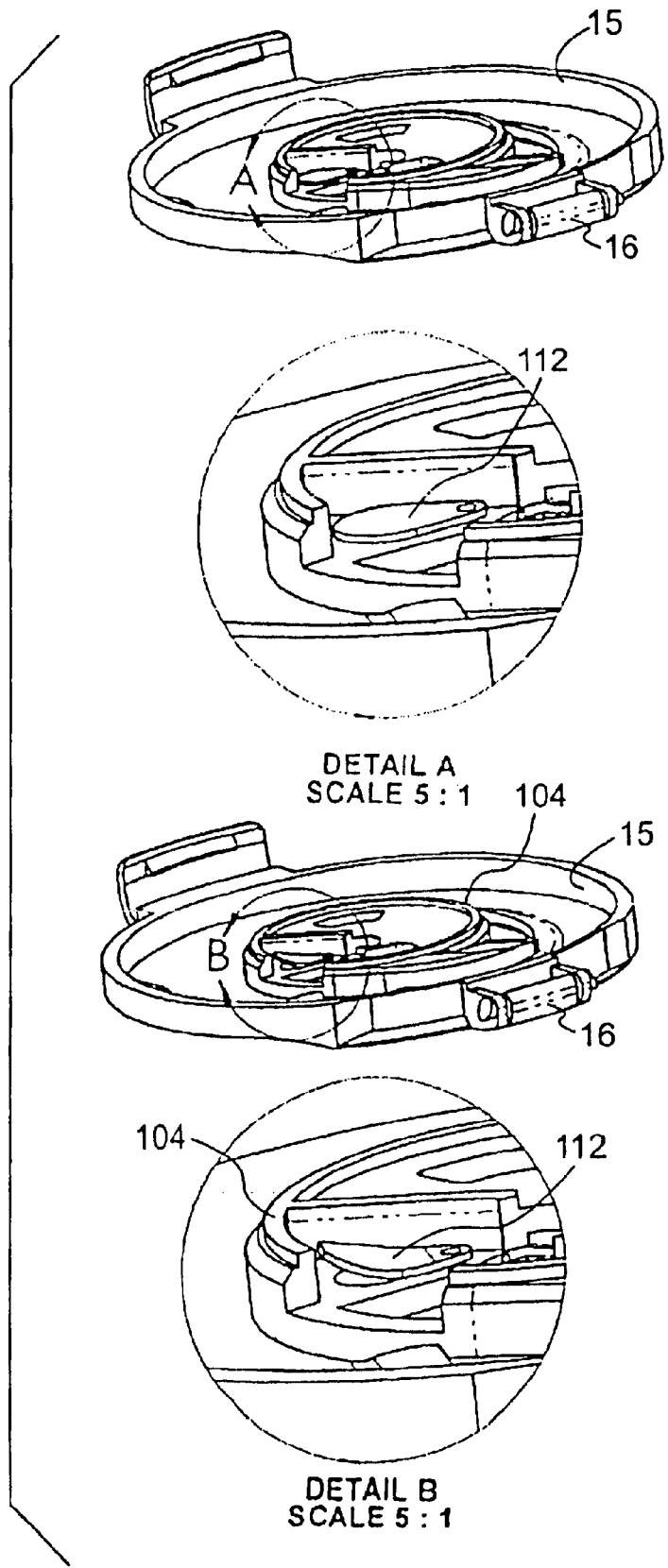

As shown in FIG. 13, the flow indicator 110 is in the form of an arcuate flag 113 that has downward projections 114, that reside in grooves 116 in the underside of the lid. As air is drawn into the inhaler 10 it causes the flag 113 to move in the grooves 116 and to rise up a ramp to assume a visible position through the area 103 of the window 100. The ramp tends to hold the flag 113 in the operative position after inhalation. When the lever 30 is indexed to the closed position, the oscillating movement of the top of the cartridge 50 causes arcuate cut-outs 117 and 118 in the top 52 of the cartridge to engage the projections 114 to return the flag 113 to the inoperative and less visible position. The incoming air current is sufficient to drive the flag 113 to the operative position. Thus, as shown in FIG. 13 the airflow is such that when the user inhales on the mouthpiece 26 air is drawn into the inhaler 10 via the air inlet 19 around the underside of the window 100 into the inhaler to move the flag 113 to the position shown in FIG. 13b. At this stage with the flag 113 in the operative position the air flows in to the inhaler displacing the one way valve 112 and into the cartridge 50. The air flows through the air inlet 45 at the top of the cartridge and out under the lidding foil that has been prized upwardly by the openers 86, 87, through the perforated layer 80 across the top of the compartment 70 and out through the radially outer section of the compartment through the perforated layer 80 and the inhalation aperture 27 and mouth piece 26. The air current is such that it causes turbulence causing the powder to be drawn through the perforated layer 80 to be entrained in the air for expulsion. The perforated layer 80 has the role of preventing escape of powder without the air current so thus, if for some reason, the lidding foil 90 is removed from the compartment by accident the perforated layer 80 prevents escape of the powder and only allows powder escape when it is entrained in an air current. The perforations in the layer 80 also assist to control the particle size of the released medicament.

The lid also includes the small viewing tab 101 that exposes through magnification an arcuate line of numbering that would be positioned on the lidding foil 90 and exposed through the hole 44 in the upper cover 52. The numbering reflects the number of recesses 70 with unused doses so that the user of the inhaler can know how many doses remain in the cartridge.

The inhaler 10 also includes a number of other features that reduce inadvertent additional dosage and reduce the likelihood of accidental displacement of the medicament. It is only on a full displacement of the lever 30 to the right as shown in FIG. 3 that opens the next dose and indexes the cartridge so the dose is positioned in line with the airflow passageway. The lever is connected to an arcuate band the drive cam 18 that locates on the inner surface of the body 11. The connection between the drive lever 30 and drive cam 18 introduces a small degree of free play or neutral movement. The lever is coupled to the drive cam having an aperture 109 so that only full displacement of the lever to the right as shown in FIG. 4 moves the aperture 109 in the drive cam 18 into correct alignment with the aperture 27 of the mouthpiece 26 to open the air passageway. When the lever returns to the left or closed position the drive cam moves to close off the mouthpiece 26.

The lever 30 that closes off the airflow passageway and does not open this passageway until the lever has again been displaced fully to the right. As the lever 30 is displaced the openers 86, 87 lift the lidding foil 90 from the perforated layer 80 to expose the radially inner and outer sections of recessed compartment 70. By the time the lever 30 has moved to the fully displaced position the foil 90 has been lifted from the radially inner and outer sections of the compartment 70 to open the air passageway. At that time the air passageway is open to the mouthpiece 26 allowing inhalation. If the lever is closed i.e. returned to its original position to the left without taking the dose that dose will then be lost because it will be indexed into an inoperative position when the lever has moved again. Thus reducing the possibility of unintentional additional dosing.

The cover 52 that is positioned over the foils 60, 80 and 90 protects doses that are not used from escape into the inhaler so that once the cartridge is discarded any residual medicament is discarded with the cartridge. Because the openers 86, 87 only lifts the lidding foil 90 off the perforated layer 80 an unadministered dose becomes effectively sealed in its recess 70 as it is indexed past the openers which allows the lidding foil to return to its former position with the bar 47 closing off the compartment 70.

The flap 112 operates as a one-way valve to ensure that exhalation does not have any effect on the medicament. The valve virtually prevents or at least minimises the amount of air that can be blown into the device so that exhalation does not dislodge or disturb a readied dose or for that matter disturb a dose that has not been administered. When in its uppermost position the one way valve 112 closes the air flow pathway exit to minimise the possibility of air flow over the unadministered dose.

The shape of the cutouts in the periphery of the base is such that when the last dose has been dispensed the lever cannot further rotate the disc so that the user becomes aware that the cartridge is empty and can thus replace the cartridge.

Figure 15:
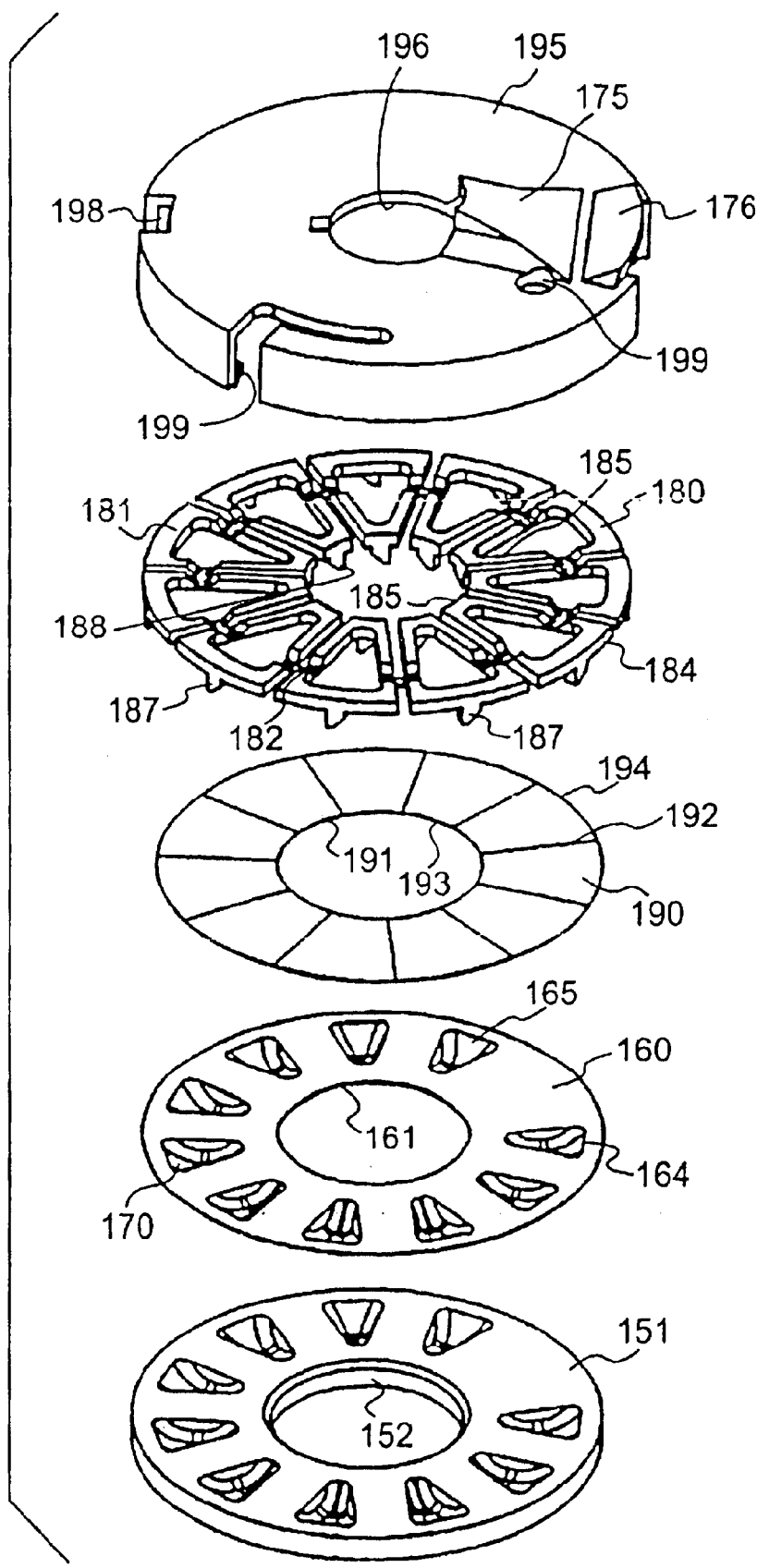
FIG. 15 is an exploded perspective view of a cartridge in accordance with a second embodiment of the invention.
Figure 16:
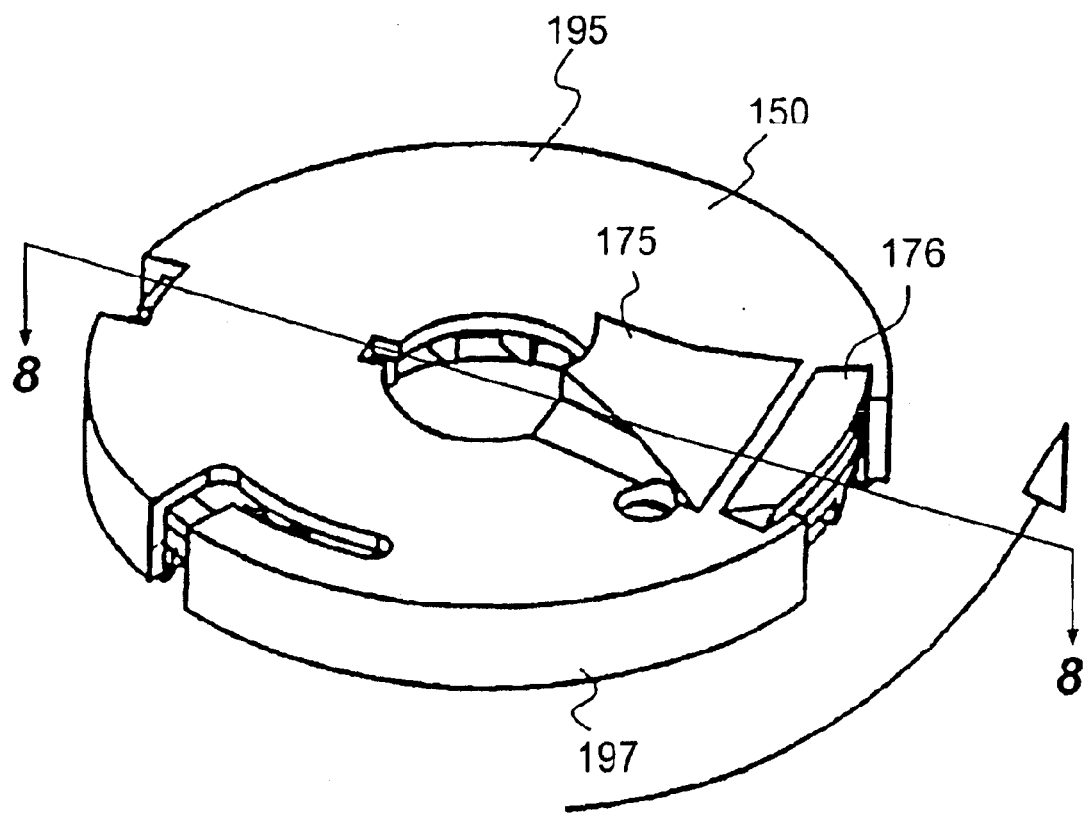
FIG. 16 is a perspective view of an upper cover of the cartridge of FIG. 15.
Figure 17:
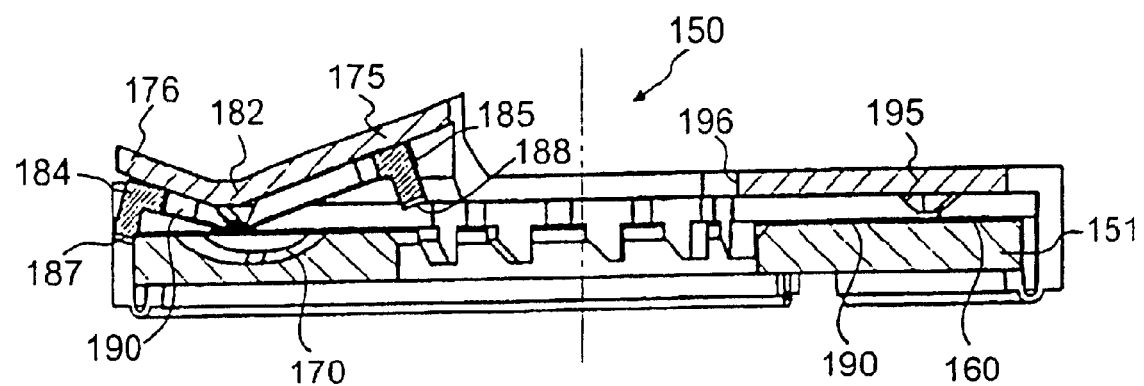
FIG. 17 is a cross sectional view taken along the lines 8—8 of FIG. 16.

FIGS. 15 to 17 illustrate a second embodiment that utilises a different cartridge which is shown in FIG. 15. The cartridge 150 has a slit top foil layer 190 provided with radial slits 192 that define segments that correspond to the position of each compartment. The top foil layer 190 has a central aperture 191 and is bonded to the lower foil 160 to seal off the compartments 170. A circular assembly 180 of flip top members 181 is bonded to the top foil 190. The assembly 180 comprises a plastics moulding in the form of a plurality of radially extending flip top members 181 that are interconnected by circumferentially extending webs 182. Each flip top member 181 comprises a radially outer arm 184 that is joined to a V-shaped inner arm 185 by the webs 182 that interconnect that flip top member 181 to the adjacent flip top members. The underside of both the radially outer and inner arms include downwardly projecting triangular shaped lugs 187 and 188. The bonding of the assembly 180 to the top foil 190 means that each segment includes a segmentally shaped piece of foil with the skeletal framework of the flip top members 181 transcribing the inner and outer circumferential edges 193 and 194 as well as the radial edges of the segment. Because the assembly 180 is bonded to the top foil 190, rotation of the disc base 151 causes rotation of the assembly 180, top foil 190 and lower foil 160 in unison relative to the cover 195.

The assembly of the disc base 151, two foil layers 160 and 190 and flip top assembly 180 is then covered by a plastics cover 195 that has a central aperture 196 and a downwardly extending annular skirt 197 that covers the components. An arcuate cutout 198 is provided in the periphery of the skirt 197 of the cover 195 through which a lever (not shown), similar to the first embodiment, can extend to engage the disc base 151. The rotation of the disc base 151 and foil layers 160 and 190 and flip top assembly 180 relative to the cover 195 is illustrated in FIG. 16. An arcuate cutout 199 is provided in the periphery of the skirt 197 of the cover 195 which, prevents the base rotating in the wrong direction by engaging the disc base 151.

Displacement of the lever rotates the disc base 151 causing the inner and outer lugs 187, 188 on the flip top member 181 to ride up on radial projections on the base of the inhaler (not shown) to cause the arms 184, 185 of the flip top members 181 to flex upwardly as shown in FIG. 17 about the central line or webs 182. Upward flexing of the flip top members 181 lifts the top foil 190 from the radially inner and outer edges of the compartments 170 causing an air passageway to form between the centre of the cartridge 150, the lifted inner flip top arm 184 the compartment 170 and the lifted outer flip top arm 185. In this way the airflow passageway is defined by the top foil 190, the flip top member 181 and the compartment 170. The cover 195 of the cartridge has inclined up standing portions 175 and 176 that are positioned to accommodate the flip top member 181 in the elevated position as shown in FIG. 17. As the disc base 151 is further rotated the undersurface of the cover 195 forces the previously opened flip top members 181 down to the horizontal position, shown around the remainder of the periphery of the flip top assembly 180 in FIG. 15. The radial slits 192 in the top foil 190 facilitate the upward movement of the flip top members 181 relative to the remainder of the foil 190.

The flip top assembly 180 has a dual role of displacing the top foil 190 layer from the lower foil 160 and thus exposing each compartment 170 whilst at the same time forming a framework for an air passageway that flows from the aperture in the top of the lid of the inhaler down through the centre of the inhaler and along the radial arms 184, 185 to pass through the end of the radial outer arm 185 and through the mouthpiece in the periphery of the body. The flip top members 181 lift the top foil 190 off the lower foil 160 and the radial edges of the compartment and the skeletal structure of the members 181 coupled with the foil surfaces provides the air passageway so that the user inhales through the mouthpiece drawing air down and into the inhaler and through the passageway. The air current picks up the powder in the exposed recess 170. The powder is then entrained in the air to leave the inhaler via the mouthpiece.

Figure 18:
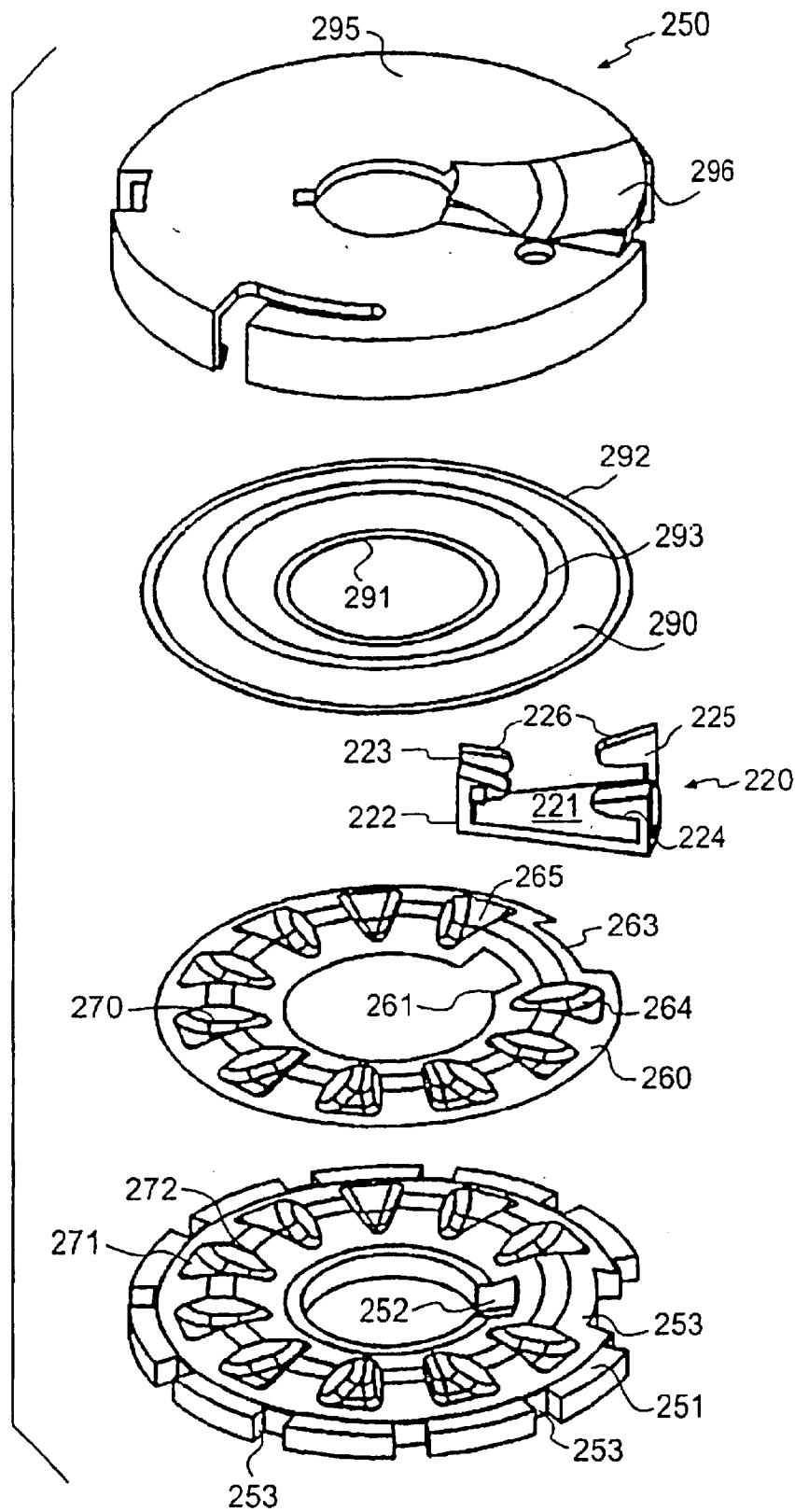
FIG. 18 is an exploded perspective view of a cartridge in accordance with a third embodiment of the invention.
Figure 19:
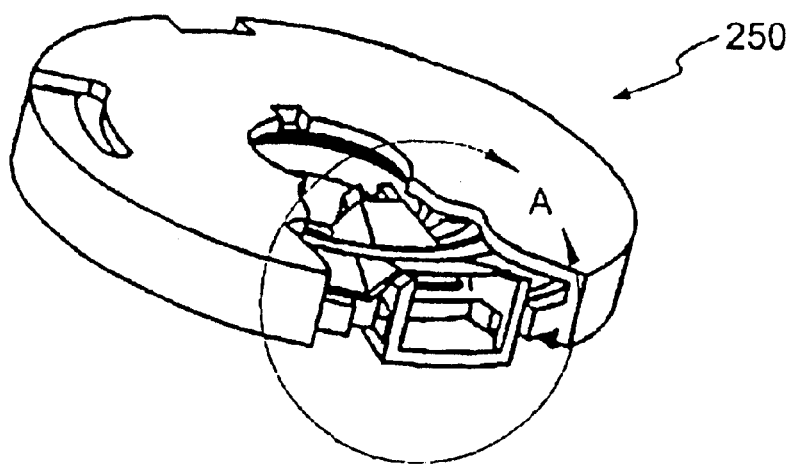
FIG. 19 is an enlarged perspective view of the mouth of the cartridge shown in FIG. 18.
Figure 19A:
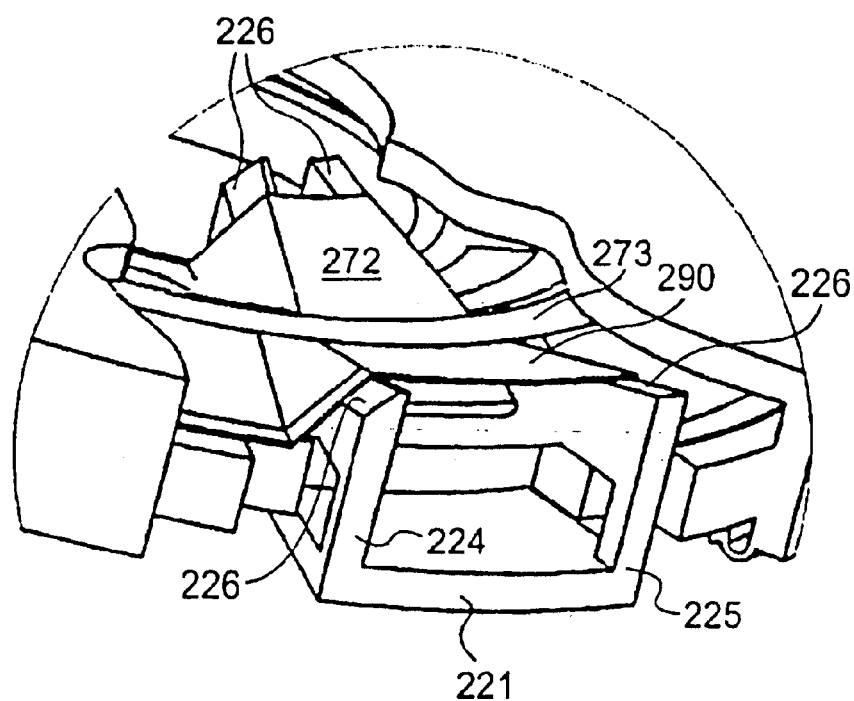

In the third embodiment shown in FIGS. 18 and 19, the disc base 251 and lower foil 260 are provided with radially inner and outer cutouts 252, 253, 262, 263 in the gap 268 between the first and last compartment 264, 265. The cut-outs 252, 253, 262, 263 accommodate a disc opener 220 in the form of a bracket having a flat base 221 terminating an upstanding posts 222, 223, 224, 225 at either end with the posts having inturned downwardly extending flanges 226. The posts and flanges 226 are positioned on the radially outer and radially inner end of the opener 220 and allow the opener to clip against the underside of the disc base 251 with the flat base 221 in parallel sliding contact with the underside of disc base 251 and the flanges 226 extending across the lower foil 260 surface but beneath the upper foil 290. The disc opener 220 is located in the cover 250 of the cartridge in a manner that it cannot rotate with the disc base 251 so that as the disc base is rotated the leading edges of the flanges 226 have the effect of lifting up the radially inner and radial edge of the top foil 290 on the adjacent compartment 270. As the disc base is indexed to the operative position as shown in FIG. 19 the radially inner and radially outer edges of the top foil 290 are lifted clear of the compartment 270 and the air passageway is defined by the compartment base and the top foil 290 that has been raised at least adjacent the radially outer and radially inner edges of the compartment by the disc opening flanges 226.

To ensure that the top foil 290 lifts off a single compartment 270 the radially outer 271 and radially inner edges 272 of each compartment 270 are at a position lower than the centre of the compartment 273 so that the disc opener flanges 226 only have to lift the radially inner 291 and radial outer 292 edges of the top foil level with the centre 293. It is for this reason that the top foil 290 is illustrated with what appear to be concentric rings. The central ring 293 allows the radially inner and radially outer sections of the top foil 290 to lift into the open position. This arrangement provides a narrow passageway whereby the central portion of the top foil 290 remains above the recessed compartment 270 and the air current to ensure that the air current is in close proximity to the powdered medicament.

When the top foil 290 is bonded to the lower foil 260 there is no bond in the gap 268 between the first 264 and last 265 compartments (except for the compartment periphery—a sealing band surrounding the compartment) which means that it becomes a simple exercise to insert the disc opening flanges 226 between the foil surfaces in that gap 268 to complete assembly.

The cover 295 of the disc 250 is provided with a raised inclined section 296 over the position of the disc opener 220 to accommodate the upstanding posts and flanges 226.

Features of the Preferred Embodiments

The inhaler is reusable, whilst the empty cartridges are discarded.

Cartridges can be supplied with a range of dose number, medicament type and volume.

Full and partially full cartridges can be loaded into and removed from the inhaler as required—either well before a dose is required or just prior to use.

Loading of the cartridge does not open a dose for inhalation.

The dose is opened and prepared for inhalation by simply sliding the indexing lever.

The access to the mouthpiece is opened or closed by simply sliding the indexing lever.

The possibility of unintentional additional dosing is minimised.

Exhalation into the inhaler does not affect the effectiveness of the next dose from the cartridge.

The inhaler via the cartridge has a "doses remaining" indicator.

The inhaler has an indicator to indicate correct dosage received.

The cartridge covers and foils protect the user from residues in opened compartments of the cartridge.

Although in the preferred embodiments the inhaler comprises an inhaler body and disposable cartridge it is understood that in a simple form the inhaler may simply be like the cartridge that is without the external body. The cartridge would include a mechanism to displace the compartments and cause opening of each compartment when it is aligned with an outlet aperture that would serve as the mouthpiece.

Medications Used With the Inhaler

The inhaler may be used to provide medications selected from the following therapy areas: anti-influenza, analgesic, anti-anginal preparation, antiallergic, anti-infective, anticancer, antihistamine, anti-inflammatory, antitussive, bronchodilator, cortiscosteroid, diuretic, anticholinergic, hormone, xanthine, osteoporosis, hypertension, therapeutic protein or peptide, vaccine, diagnostic agent or gene therapy agent.

The inhaler may be used to provide medications selected from the following group: zanamivir, codeine, dihydromorphine, ergotamine, fentanyl, morphine, diltiazem, cromoglycate, ketotifen, nedocromil, cephalosporins, penicillins, streptomycin, sulphonamides, tetracyclines, pentamidine, methapyrilene, beclomethasone dipropionate, fluticasone propionate, flunisolide, budesonide, rofleponide, mometsasone furoate, triamcinolone acetonide, noscapine, albuterol sulphate, salmeterol xinafoate, salmeterol, ephedrine, adrenaline, fenoterol, formoterol, isoprenaline, metaproterenol, phenylephrine, phenylpropanolamine, pirbuterol acetate, reproterol hydrochloride, rimiterol, terbutaline sulphate, isoetharine, tulobuterol, orciprenaline, adenosine 2a agonists, α4 integrin inhibitors, amiloride, ipratropium, tiotropium, atropine or oxitropium, cortisone, hydrocortisone or prednisolone, aminophylline, choline theophyllinate, lysine theophyllinate or theophylline, insulin or glucagon, or salts, esters, or solvates thereof, alone or in combination.

What is claimed is:

1. An inhaler for delivering metered doses of powdered medicament, the inhaler comprising a plurality of compartments spaced in an array and containing a metered dose of the medicament, a lever to displace the compartments one by one into line with an inhalation aperture of a mouthpiece, wherein the plurality of compartments include inner and outer edges, wherein the plurality of compartments are closed by a sealing layer secured to the compartments, and wherein the inhaler further includes a mechanism adapted to lift first and second spaced portions of the sealing layer off the inner and outer edges of at least one compartment of the plurality of compartments while leaving an intermediate portion of the sealing layer, between the first and second portions, secured to the at least one compartment to open an air passageway defined by the at least one compartment and the intermediate portion of the sealing layer secured to the at least one compartment so that, in use, on inhalation through the mouthpiece, air flows in the air flow passageway in contact with the intermediate portion and picks up and entrains the powder in the at least one compartment to be drawn with the air out of the inhaler through the mouthpiece.

2. The inhaler according to claim 1 wherein the compartments are spaced in an annular array and the means to lift the sealing layer lifts the inner and outer edges of the sealing layer.

3. The inhaler according to claim 1 wherein each compartment is covered by a perforated layer and the sealing layer covers the perforated layer with the lifting means lifting the inner and outer edges of the sealing layer from the perforated layer.

4. The inhaler according to claim 1 wherein the lever is moveable from an inoperative position to an operative position in which one compartment is indexed to align with the inhalation aperture and the inner and outer edges of the sealing layer are lifted off the compartment, the lever being returnable to the operative position.

5. The inhaler according to claim 4 wherein the inhaler has a sealing bar that pushes down the sealing layer at the inner and outer edges of the at least one compartment as the lever is returned to the inoperative position.

6. The inhaler according to claim 5 wherein the body defines a compartment into which the cartridge is located, a lid being pivoted to the body to close off the compartment.

7. The inhaler according to claim 6 wherein the lid includes an air entry aperture.

8. The inhaler according to claim 7 wherein the lid includes indicator means to provide a visual indication that air has been drawn through the inhaler.

9. The inhaler according to claim 8 wherein the indicator means comprises a member displaceable in response to a minimum air flow.

10. The inhaler according to claim 9 wherein the member is displaceable from a start position to a finish position, the finish position reflecting minimum air flow.

11. The inhaler according to claim 5 wherein the cartridge comprises a disc assembly mounted within upper and lower covers, the disc assembly being axially rotatable relative to the lower cover.

12. The inhaler according to claim 11 wherein the disc assembly comprises the array of spaced compartments sealed by a disc shaped sealing layer.

13. The inhaler according to claim 12 wherein the array of compartments are formed in a metal foil disc shaped sheet that is positioned on a similarly formed disc shaped base member.

14. The inhaler according to claim 11 wherein the lower cover has a pair of spaced projections that extend past slots in the disc assembly to engage the underside of the sealing layer whereby rotation of the disc assembly past the projections causes the projections to lift the sealing layer off the inner and outer edges of the compartments one by one as the compartments move over the projections.

15. The inhaler according to claim 11 wherein the member is displaceable from a start position to a finish position, the finish position reflecting minimum air flow, and wherein the upper cover is capable of oscillating relative to the lower cover, the oscillation causing rotation of the member to the start position.

16. The inhaler according to claim 1 wherein the inhaler comprises a body adapted to receive a cartridge that carries the compartments, the inhalation aperture being provided in the body in a position aligned with an outlet aperture in the cartridge, and the lever being mounted on the body to be displaceable from the inoperative position to the operative position in which a fresh compartment is displaced and opened so that the opened compartment is aligned with the inhalation aperture.

17. The inhaler according to claim 16 wherein the lever includes a component that closes the inhalation aperture in the inoperative position and opens the aperture in the operative position.

18. The inhaler according to claim 1 wherein the mechanism comprises a flip top member secured to the sealing layer and having portions adapted to flex upwardly relative to the compartment to lift the sealing layer off the inner and outer edges of the compartment.

19. The inhaler according to claim 18 wherein the inhaler includes means to flex the portions upwardly as the compartment is displaced relative to the inhaler.

20. The inhaler according to claim 1 wherein the mechanism comprises an opener in the form of wedge shaped members mounted spaced apart on a plate which is positioned beneath the array of compartments, the wedge shaped members engaging the underside of the sealing layer, the plate being fixed relative to the inhaler so that displacement of the array of compartments relative to the inhaler causes each compartment to move past the wedge shaped members to lift the sealing layer off the inner and outer edges of the compartment.

21. The inhaler according to claim 1 wherein the inhaler has a one way valve that allows air to be drawn in through the inhaler and out of the mouthpiece but prevents flow of air in the reverse direction.

22. The inhaler according to claim 1 wherein ten compartments are spaced in an array.

23. The inhaler according to claim 1, wherein the portion of the sealing layer secured to the at least one compartment is secured to at least a portion of a periphery of the at least one compartment.

24. The inhaler according to claim 1, wherein the sealing layer is secured to at least a portion of peripheries of the plurality of compartments, and wherein the mechanism adapted to lift the sealing layer off the inner and outer edges of the at least one compartment is further adapted to leave a portion of the sealing layer secured to a portion of the periphery of the at least one compartment after the sealing layer is lifted.

25. The inhaler according to claim 1, wherein the sealing layer is secured to at least portions of peripheries of the plurality of compartments, and wherein the mechanism adapted to lift the sealing layer is adapted to lift radially inner and outer edges of the sealing layer while leaving a portion of the sealing layer secured to the at least one compartment to define the air passageway.

26. The inhaler according to claim 1, wherein the sealing layer comprises a sheet foil.

27. The inhaler according to claim 1, wherein the sealing layer comprises a sheet with an interior edge and an exterior edge, wherein the mechanism adapted to lift the sealing layer off the at least one compartment is adapted to lift a portion of the interior edge and a portion of the exterior edge of the sealing layer while leaving a portion of the sealing layer in contact with the compartment.

28. The inhaler according to claim 27, wherein the interior edge is formed by a hole through the sheet.

29. The inhaler according to claim 1, wherein the sealing layer comprises an annular sheet, wherein the mechanism adapted to lift the sealing layer is adapted to lift a portion of the radially inner edge and a portion of the radially outer edge of the sealing layer while leaving a portion of the sealing layer in contact with the compartment.

30. A disposable cartridge adapted to be received in a body of an inhaler, the cartridge having a plurality of compartments spaced in an array and each arranged to contain a metered dose of medicament, the compartments being displaceable one by one into line with an outlet aperture, each compartment including inner and outer edges secured to the compartments, the plurality of compartments being closed by a sealing layer, and a mechanism adapted to lift first and second spaced portions of the sealing layer off the inner and outer edges of at least one compartment of the plurality of compartments while leaving an intermediate portion of the sealing layer between the first and second portions secured to the at least one compartment to open an air passageway defined by the at least one compartment and the intermediate portion of the sealing layer secured to the at least one compartment so that, in use, air flows in the air flow passageway in contact with the intermediate portion and picks up and entrains the powder in the at least one compartment to be drawn with the air out of the cartridge through the outlet aperture.

31. The disposable cartridge of claim 30, wherein the compartments are spaced in an annular array and the mechanism adapted to lift the sealing layer lifts the inner and outer edges of the sealing layer.

32. The disposable cartridge of claim 30, wherein each compartment is covered by a perforated layer and the sealing layer covers the perforated layer, and wherein the mechanism adapted to lift the sealing layer is further adapted to lift the inner and outer edges of the sealing layer from the perforated layer.

33. The disposable cartridge of claim 30, further comprising a sealing bar adapted to push down the sealing layer at the inner and outer edges of at least one compartment as the compartments are displaced.

34. The disposable cartridge of claim 30, wherein the cartridge comprises a disc assembly mounted within upper and lower covers, the disc assembly being axially rotatable relative to the lower cover.

35. The disposable cartridge of claim 34, wherein the disc assembly comprises the array of spaced compartments sealed by a disc shaped sealing layer.

36. The disposable cartridge of claim 30, comprising a pair of spaced projections that extend past slots in the array to engage the underside of the sealing layer and adapted lift the sealing layer off the inner and outer edges of the compartments one by one as the compartments move over the projections during displacement of the compartments.

37. An inhaler for delivering metered doses of powdered medicament, the inhaler comprising a body adapted to receive a disposable disc shaped cartridge, the cartridge having a plurality of compartments spaced in an annular array and each arranged to contain a metered dose of the medicament, a lever to displace the compartments one by one into line with an inhalation aperture positioned in the body to constitute a mouthpiece, each compartment including inner and outer edges, the plurality of compartments being closed by a sealing layer secured to the compartments, the inhaler also being provided with a mechanism adapted to lift first and second spaced portions of the sealing layer off the inner and outer edges of at least one compartment of the plurality of compartments while leaving an intermediate portion of the sealing layer between the first and second portions secured to the at least one compartment to open an air passageway defined by the inner and outer edges, the at least one compartment and the intermediate portion of the sealing layer secured to the at least one compartment so that, in use, on inhalation through the mouthpiece, air flows in the air flow passageway in contact with the intermediate portion and picks up and entrains the powder in the at least one compartment to be drawn with the air out of the inhaler through the mouthpiece.

38. An inhaler for delivering metered doses of powdered medicament, the inhaler comprising:
   a plurality of compartments spaced in an array and containing a metered dose of the medicament,
   a displacement mechanism adapted to displace the compartments to be in airflow communication with the inhalation aperture, wherein
      each of the plurality of compartments includes a first and a second edge, wherein
         each of the plurality of compartments is closed by a sealing layer secured to the compartments, and wherein
   the inhaler further includes a mechanism adapted to lift first and second spaced portions of the sealing layer off the inner and outer edges of at least one compartment of the plurality of compartments while leaving an intermediate portion of the sealing layer, between the first and second portions, secured to the at least one compartment to open an air passageway defined by the at least one compartment and the intermediate portion of the sealing layer secured to the at least one compartment so that, in use, on inhalation through the inhalation aperture, air flows in the air flow passageway in contact with the intermediate portion and picks up and entrains the powder in the at least one compartment to be drawn with the air out of the inhaler through the inhalation aperture.

39. An inhaler for delivering metered doses of powdered medicament comprising:
   a body adapted to receive a cartridge, the cartridge comprising a plurality of compartments spaced in an array and containing a metered dose of medicament, the compartments being sealed by a sealing layer in contact with said compartments;
   an inhalation aperture positioned in the body and adapted to substantially interface with a human mouth;
   an opening mechanism adapted to remove the sealing layer from a compartment in at least two separate locations while leaving an intermediate portion of the sealing layer between one of said separate locations and another of said separate locations remaining in contact with the compartment so as to open an air passageway extending from said one separate location, through the compartment, to said another separate location, the passageway being defined by the compartment and said intermediate portion of the sealing layer remaining in contact with the compartment; and a displacement mechanism adapted to displace the compartments serially in reference to the inhalation aperture so that at least one of the removed locations is in airflow communication with the aperture; wherein the inhaler is adapted so that on inhalation through the aperture, air flows through the air flow passageway in contact with said intermediate portion and picks up and entrains the medicament in the compartment to be drawn with the air out of the inhaler through the aperture.

40. The inhaler of claim 39, wherein the compartments are covered by a perforated mesh.

41. The inhaler of claim 39, wherein the passageway consists of the compartment and the sealing layer.

42. The inhaler of claim 41, wherein the compartments are covered by a perforated mesh.

43. The inhaler of claim 42, wherein the sealing layer covers the perforated mesh, and wherein the opening mechanism is adapted to separate the sealing layer from the perforated mesh.

44. The inhaler of claim 39, wherein the opening mechanism comprises at least two projections that engage the sealing layer between the material of the compartments and the sealing layer, and wherein upon movement of the compartments relative to the projections, the sealing layer is removed from the compartment material in said at least two locations thereby opening the airflow passageway.

45. The inhaler of claim 44, wherein the inhaler is adapted so that the compartments not in communication with the aperture are substantially sealed.

46. The inhaler of claim 44, wherein the compartments are spaced in a circular array.

47. The inhaler of claim 46, wherein the compartments are arranged in a compartment disk, wherein the compartment disk has slots adapted to permit the disk to pass by the projections and thus permit the projections to interface with the sealing layer when the disk is placed into the cartridge.

48. The inhaler of claim 47, wherein the compartment disk is mounted on a base member, the base member having substantially similar slots as the compartment disk.

49. The inhaler of claim 47, wherein the compartment disk is adapted to rotate, wherein as the compartment disk rotates, the sealing layer is removed from the compartment disk in the vicinity of the projections.

50. The inhaler of claim 49, wherein the removal of the sealing layer from the compartment disk occurs in the vicinity of radial inner and radial outer edges of the compartment disk.

51. The inhaler of claim 39, wherein the displacement mechanism is a lever.

52. The inhaler of claim 39, further comprising a closing mechanism adapted to substantially seal compartments that have been unsealed and are no longer in communication with the aperture.

53. The inhaler of claim 39, further comprising an indicator adapted to provide a user with an indication that air has been drawn through the aperture.

54. The inhaler of claim 39, further comprising an indicator adapted to provide a user with an indication that a sufficient dosage of the medicament has been removed from the compartment.

55. The inhaler of claim 39, further comprising a valve adapted to effectively prevent air from being blown through the inhaler in a reverse direction.

56. A disposable cartridge for an inhaler for delivering metered doses of powdered medicament comprising:

a plurality of compartments spaced in an array and containing a metered dose of medicament, the compartments being sealed by a sealing layer;

an opening mechanism adapted to remove the sealing layer from a compartment in at least two separate locations while leaving an intermediate portion of the sealing layer between one of said separate locations and another of said separate locations remaining in contact with the compartment so as to open an air passageway extending from said one separate location, through the compartment, to said another separate location, the passageway being defined by the compartment and said intermediate portion of the sealing layer remaining in contact with the compartment; and the cartridge is adapted to be attached to and removed from an inhaler body, wherein the compartments are adapted to be serially displaceable in reference to an outlet location for the medicament on the cartridge so that at least one of the removed locations is in airflow communication with the inhaler, and wherein the cartridge is adapted so that air flows through the air flow passageway in contact with the intermediate portion so as to pick up and entrain the medicament in the compartment to be drawn with the air out of the compartment.

57. The cartridge of claim 56, wherein the compartments are covered by a perforated mesh.

58. The cartridge of claim 56, wherein the passageway consists of the compartment and the sealing layer.

59. The cartridge of claim 58, wherein the compartments are covered by a perforated mesh.

60. The cartridge of claim 56, wherein the opening mechanism comprises at least two projections that engage the sealing layer between the material of the compartments and the sealing layer, and wherein upon movement of the compartments relative to the projections, the sealing layer is removed from the compartment material in at least two locations thereby opening an airflow passageway.

61. The cartridge of claim 60, wherein the cartridge is adapted so that the compartments not in communication with the aperture are substantially sealed.

62. The cartridge of claim 60, wherein the compartments are spaced in a circular array.

63. The cartridge of claim 62, wherein the compartments are arranged in a compartment disk, wherein the compartment disk has slots adapted to permit the disk to pass by the projections and thus permit the projections to interface with the sealing layer when the disk is placed into the cartridge.

64. The cartridge of claim 63, wherein the compartment disk is mounted on a base member, the base member having substantially similar slots as the compartment disk.

65. The cartridge of claim 63, wherein the compartment disk is adapted to rotate, wherein as the compartment disk rotates, the sealing layer is removed from the compartment disk in the vicinity of the projections.

66. The inhaler of claim 65, wherein the removal of the sealing layer from the compartment disk occurs in the vicinity of the radial inner and radial outer edges of the compartment disk.

* * * * *